United States Patent [19]
Colvin, Jr.

[11] Patent Number: 5,910,661
[45] Date of Patent: Jun. 8, 1999

[54] FLOURESCENCE SENSING DEVICE

[76] Inventor: Arthur E. Colvin, Jr., 12321 Middlebrook Rd., Germantown, Md. 20874

[21] Appl. No.: 08/855,235

[22] Filed: May 13, 1997

[51] Int. Cl.⁶ .................................................. G01N 15/06
[52] U.S. Cl. ...................... 250/573; 250/227.14; 356/436
[58] Field of Search ............................ 250/573, 227.14, 250/559.4, 226, 483.1; 356/436, 437, 39, 40; 422/82.07, 82.08, 83, 88; 436/136, 137, 167, 172

[56] References Cited

U.S. PATENT DOCUMENTS

| | | | |
|---|---|---|---|
| 4,755,667 | 7/1988 | Marsoner et al. | 250/227.14 |
| 4,872,759 | 10/1989 | Stich-Baumeister et al. | 356/432 |
| 5,043,286 | 8/1991 | Khalil et al. | 250/227.14 |
| 5,517,313 | 5/1996 | Colvin, Jr. | 356/417 |

FOREIGN PATENT DOCUMENTS

| | | |
|---|---|---|
| 263805 | 4/1988 | European Pat. Off. . |
| 298333 | 1/1989 | European Pat. Off. . |
| 9706422 | 2/1997 | WIPO . |

OTHER PUBLICATIONS

Colvin, Jr., A.E., et al., "A Novel Solid–State Oxygen Sensor," *Johns Hopkins APL Technical Digest*, vol. 17, No. 4, pp. 377–385 (1996). (Month unknown).

*Primary Examiner*—Que T. Le
*Attorney, Agent, or Firm*—Rothwell, Figg, Ernst & Kurz

[57] ABSTRACT

A fluorescence sensing device for determining the presence or concentration of an analyte in a liquid or gaseous medium is constructed of an optical filter, which is positioned on a photodetector and which has a thin film of analyte-permeable, fluorescent indicator molecule-containing material on its top surface. An edge-emitting, light-emitting P-N junction is positioned on the top surface of the optical filter such that the P-N junction from which light is emitted is positioned within the film. Light emitted by the fluorescent indicator molecules impacts the photodetector thereby generating an electrical signal that is related to the concentration of the analyte in the liquid or gaseous medium. Fluorescence sensing devices according to this invention are characterized by very compact sizes, fast response times and high signal-to-noise ratios.

11 Claims, 3 Drawing Sheets

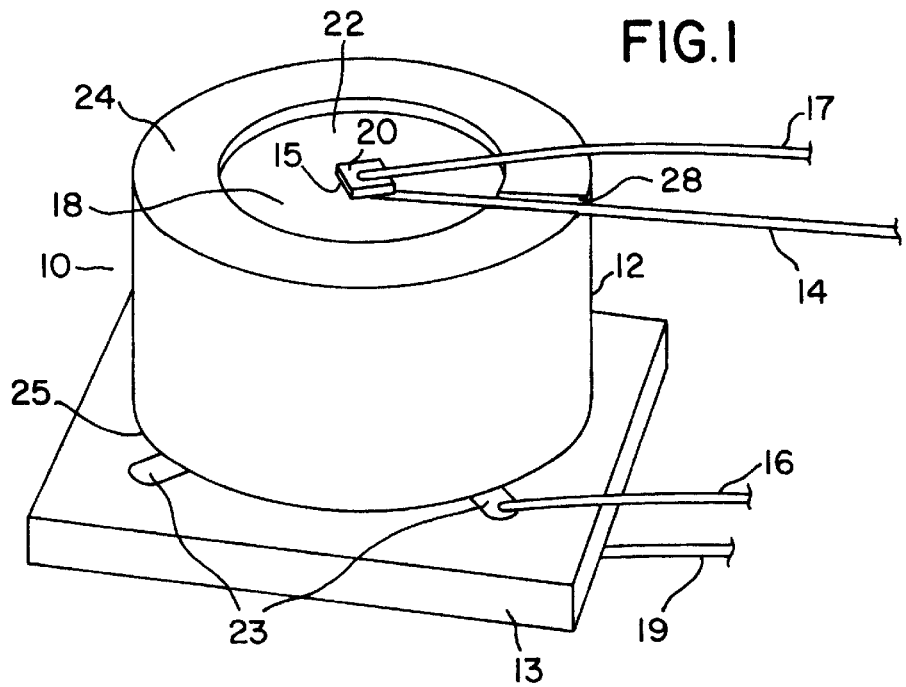
FIG.1
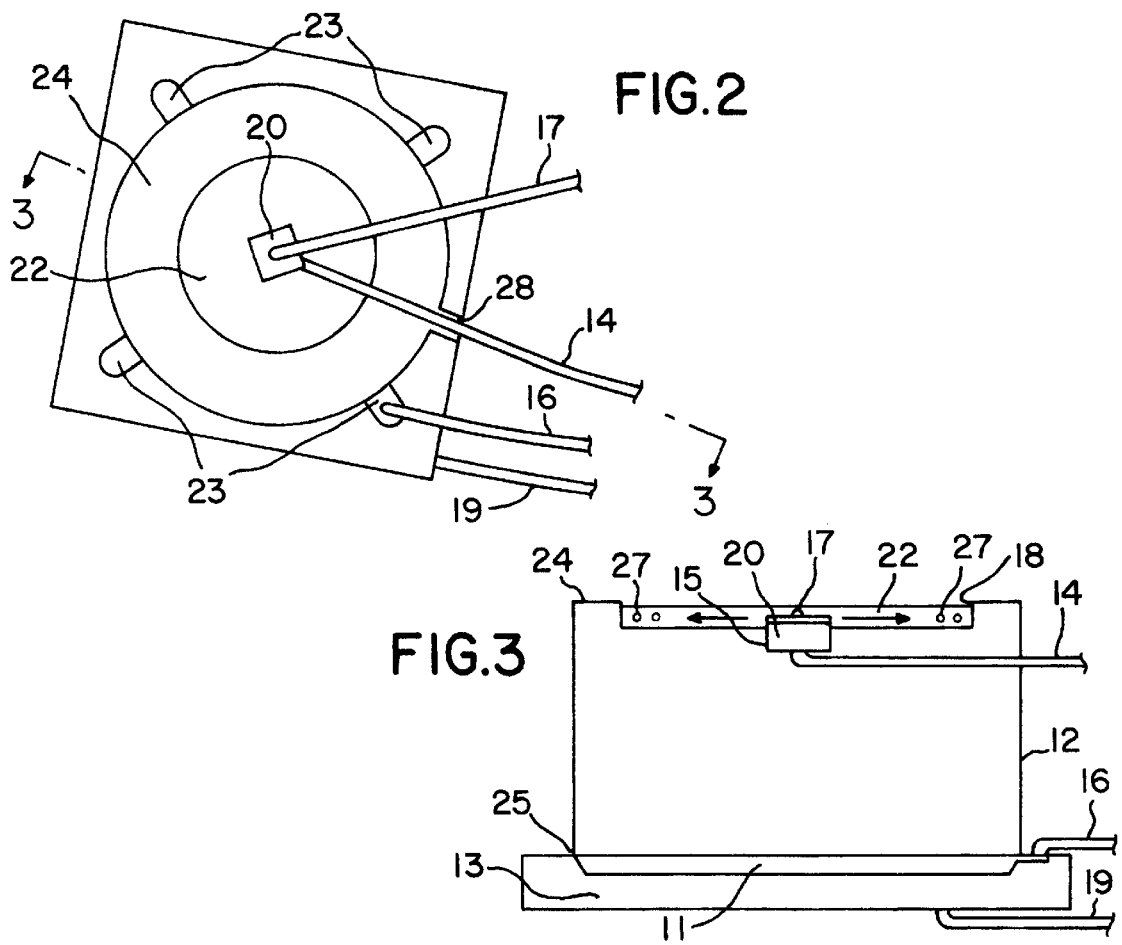
FIG.2
FIG.3

FLOURESCENCE SENSING DEVICE

BACKGROUND OF THE INVENTION

1. Field of Invention

This invention relates to an electro-optical sensing device for detecting the presence or concentration of an analyte in a liquid or gaseous medium. More particularly, the invention relates to a fluorescence sensing device which is characterized by a compact size, fast response times and high signal-to-noise ratios.

2. Background Art

U.S. Pat. No. 5,517,313, the disclosure of which is incorporated herein by reference, describes a fluorescence sensing device comprising a layered array of a fluorescent indicator molecule-containing matrix (hereafter "fluorescent matrix"), a high-pass filter and a photodetector. In this device, a light source, preferably a light-emitting diode ("LED"), is located at least partially within the indicator material, such that incident light from the light source causes the indicator molecules to fluoresce. The high-pass filter allows emitted light to reach the photodetector, while filtering out scattered incident light from the light source.

The fluorescence of the indicator molecules employed in the device described in U.S. Pat. No. 5,517,313 is modulated, e.g., attenuated or enhanced, by the local presence of the analyte. For example, the orange-red fluorescence of the complex, tris(4,7-diphenyl-1,10-phenanthroline)ruthenium(II) perchlorate is quenched by the local presence of oxygen. This complex can, therefore, advantageously be used as the indicator molecule of an oxygen sensor. Similarly, other indicator molecules whose fluorescence is affected by specific analytes are known.

In the sensor described in U.S. Pat. No. 5,517,313, the material which contains the indicator molecule is permeable to the analyte. Thus, the analyte can diffuse into the material from the surrounding test medium, thereby affecting the fluorescence emitted by the indicator molecules. The light source, indicator molecule-containing material, high-pass filter and photodetector are configured such that at least a portion of the fluorescence emitted by the indicator molecules impacts the photodetector, generating an electrical signal which is indicative of the concentration of the analyte in the surrounding medium.

While the sensing device described in U.S. Pat. No. 5,517,313 represents a marked improvement over prior art devices, there remains a need for sensors that are even more compact, less expensive and which have superior sensing characteristics to those described therein. Thus, it is an object of the present invention to provide an improvement to the sensing devices described in the aforementioned patent.

BRIEF DESCRIPTION OF THE DRAWINGS

The invention will be illustrated by reference to the accompanying drawings in which:

FIG. 1 is a perspective view of a sensing device in accordance with the present invention;

FIG. 2 is a top plan view of the sensing device shown in FIG. 1;

FIG. 3 is a cross-sectional view of the sensing device shown in FIG. 1, taken along lines 3—3 of FIG. 2;

SUMMARY OF THE INVENTION

Figure 4:
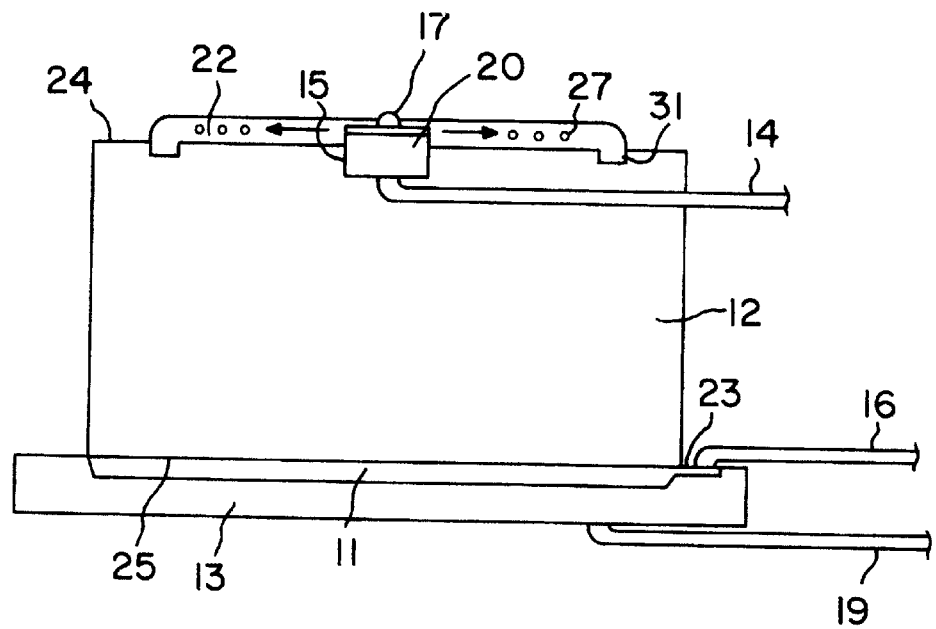
FIG. 4 is a cross-sectional view of an alternative embodiment of a sensing device in accordance with the present invention.

In accordance with the present invention, a fluorescence sensing device for determining the presence or concentration of an analyte in a liquid or gaseous medium comprises (a) an optical filter having substantially flat, parallel top and bottom surfaces;

(b) a film of analyte-permeable fluorescent matrix on the top surface of the optical filter, said fluorescent matrix containing fluorescent indicator molecules whose fluorescence is modulated by the presence of analyte in said film;

(c) a light-emitting P-N semiconductor junction which emits light at a wavelength that excites fluorescence in the indicator molecules; said light-emitting P-N junction being positioned on the top surface of the optical filter such that at least a portion of the the light is emitted within the fluorescent matrix in directions at least a portion of which are parallel to the top surface of the optical filter; and (d) a photodetector on the bottom surface of the optical filter which generates an electrical signal responsive to fluorescent light emitted by said fluorescent indicator molecules;

wherein the optical filter has a relatively low absorbance for fluorescent light emitted by said fluorescent indicator molecules and a relatively high absorbance for light emitted by said light-emitting diode.

The fluorescence sensor of the present invention is an improvement on the embodiments illustrated in U.S. Pat. No. 5,517,313. The sensors of this invention are very compact in size and have short response times and good signal-to-noise ratios.

DETAILED DESCRIPTION OF THE INVENTION

A fluorescent sensing device in accordance with this invention is shown in perspective view in FIG. 1. Sensor 10 comprises an optical filter 12. This optical filter is made of a selectively transparent material, such as doped optical glass, and has a wavelength cutoff such that it transmits light emitted from fluorescent indicator molecules employed in the device while absorbing light emitted from the light source. Suitable filters may be prepared, for example from the RG series of optical glass available from O.I. Schott, Southbridge, Mass. USA. Optical filter 12 has generally flat, parallel top and bottom surfaces 24 and 25, respectively. In one embodiment, top surface 24 has a recessed area 18, which may be machined, e.g., by laser ablation, or molded into the optical filter.

The recessed area 18 is filled with fluorescent matrix 22. This matrix is permeable to the analyte, so that analyte molecules can diffuse into and out of it at a rate related to the concentration of the analyte in the surrounding liquid or gaseous medium. This matrix is preferably a polymer which can be cast into a thin film, deposited as a film through evaporation or polymerized from monomers or oligomers in situ. Such polymer is optically transmissive at the wavelengths of excitation and emission of the indicator molecules and does not react deleteriously with the fluorescent indicator molecules or the analyte.

A variety of polymers can be used for preparation of fluorescent matrix 22. A polymer system that has been found useful for preparing oxygen sensors employs silicone polymer RTV 118, available from the General Electric Company, Pittsfield, Mass. USA. This polymer may be dissolved in a 1:1 to 1:6 petroleum ether/chloroform mixture. The fluorescent indicator ruthenium complex referred to above may be blended into the polymer solution at a concentration of from about 0.1 to 1 mM and the resulting mixture applied to the top surface 24 of optical filter 12. Evaporation of the solvents results in deposition of a fluorescent matrix film 22 on top surface 24.

The light source employed in the sensors of this invention is a light-emitting P-N junction. Such devices are well known. Upon application of an electrical potential across the P-N junction, light is emitted in directions such that at least a portion is in the same plane as the junction. The P-N junction may be provided in a variety of configurations. For convenience it will be described hereafter as a conventional light-emitting diode ("LED").

Figure 5:
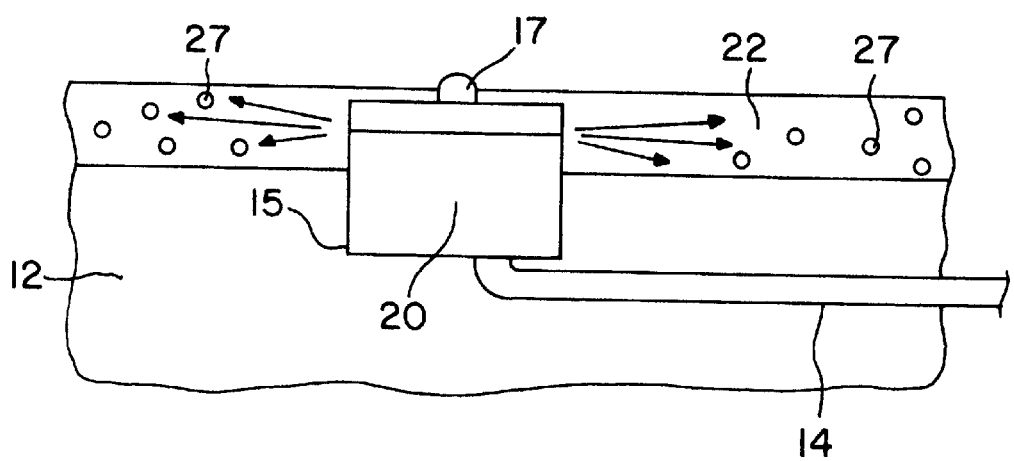
FIG. 5 is an enlarged cross-sectional view of the LED light source and surrounding structure of the sensing device shown in FIG. 1.

As best illustrated in FIG. 3, LED 20 is advantageously positioned in a pocket 15 in the upper surface of optical filter 12. Electrical leads 14 and 17 are attached to the anode and cathode of LED 20, which in turn are connected to a suitable power supply (not shown). As shown in FIG. 1, groove 28 may be cut into optical filter 12 to accomodate lead 14. The LED may be extremely small, typically having a dimension of about 200 to 300 microns on an edge. The LED is positioned on the top surface of optical filter 12 such that the P-N junction is at about the center of the thickness of the fluorescent matrix film 22. Since, as illustrated in FIGS. 3 and 5, the LED emits light substantially from its edges, the light radiates outwardly from the LED, and at least a portion of the light is emitted in directions generally parallel to top surface 24 of optical filter 12. Thus, excitation light emitted by LED 20 passes through the fluorescent indicator molecule-containing material 22 and may be absorbed by an indicator molecule 27, causing it to fluoresce.

Figure 6:
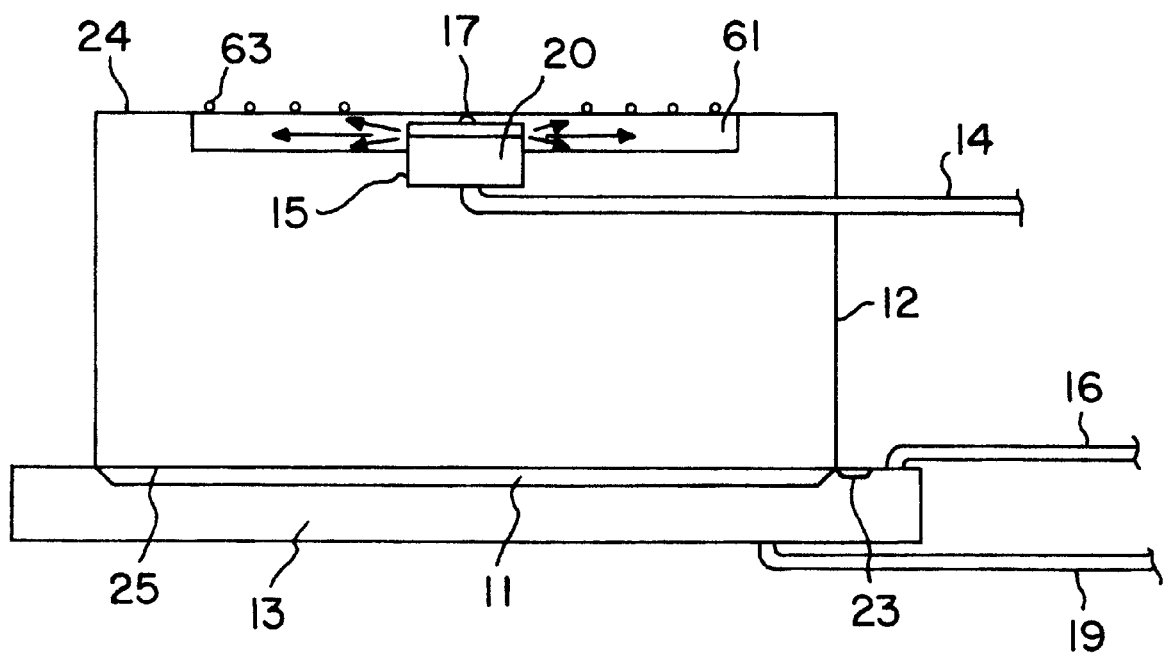
FIG. 6 is a cross-sectional view of another alternative embodiment of a sensing device in accordance with the present invention.

In an alternative embodiment illustrated in FIG. 6, a waveguide material 61 may be substituted for fluorescent matrix 22. In this embodiment, fluorescent indicator molecules 63 are positioned on the surface of waveguide material 61, such that they may be placed in contact with the liquid or gaseous test medium. Light emitted from LED 20 is largely propagated within waveguide 61 through internal reflectance. Light reflected from the interface of the waveguide material and the surrounding medium passes far enough through the surface of the material to impact a fluorescent indicator molecule 63 deposited on the surface, thereby exciting analyte-concentration dependent fluorescence in the indicator molecule.

The waveguide material is prepared from a transparent material having a refractive index substantially higher than that of the liquid or gaseous medium with which it is in contact. A suitable material is, for example, clear acrylic polymer. When a waveguide material is used in place of the fluorescent matrix, it need not be permeable to the analyte, since the fluorescent indicator molecules are positioned on the surface of the waveguide material. Any of the physical embodiments described in connection with the fluorescent matrix material may also be employed with the waveguide embodiment.

Light emitted from the indicator molecules is transmitted through optical filter 12 (and through waveguide 61, if present) and is detected by photodetector 13. Photodetector 13 advantageously has a photosensitive area 11 that corresponds in size and shape to bottom surface 25 of optical filter 12. This photosensitive area may be created by well-known photomasking and infusion doping procedures. Electrical connections 23 may be positioned outside photosensitive area 11. The photodetector produces an electrical signal in response to the amount of fluorescent light impacting it, and this signal is transmitted by electrical leads 16 and 19 to suitable amplification and measuring circuitry (not shown). As an alternative to lead 19, the bottom surface of photodetector 13 may be placed in electrical contact with a printed circuit board, e.g., by means of an electrically conductive adhesive.

Optical filter 12 and photodetector 13 may be mechanically joined with a suitable optical adhesive. Such adhesive provides a bond between the components, but does not absorb significant quantities of fluorescent light passing through the optical filter. A suitable adhesive is available as Epotek™ No. 377 from Epoxy Technology, Bilerica, Mass. USA.

The fluorescence sensors of this invention may be very compact in size. While optical filter 12 may vary substantially in depth and diameter, in a typical sensor, the diameter of the optical filter is about 0.1 inch and its depth is about 0.15 inch.

The structure of these devices permits the use of thin films of indicator molecule-containing materials. The thickness of the film advantageously ranges from about 500 Å to about 200 microns, preferably from about 10 microns to about 100 microns, most preferably from about 10 microns to about 20 microns. In the embodiment illustrated in FIG. 1, the depth of recess 18 may be used to establish a uniform and reproducible film depth. Alternatively, a controlled amount of a solution of an indicator molecule-containing polymer or monomer mixture may be applied to top surface 24 of optical filter 12, and surface tension may be employed to control the depth of the film. In the embodiment shown in FIG. 4, a moat 31 is cut into top surface 24. This moat stops the spread of the polymer while it is in the liquid state and ensures a uniform film depth. In this embodiment, uniform and reproducible film depths may be achieved by applying the indicator molecule-containing material in the liquid state with a precision micropipette or syringe.

The thinness of the film of the indicator molecule-containing material and the use of an edge light-emitting P-N junction embedded in fluorescent matrix film 22 provides unique and advantageous characteristics to the devices of this invention. The response times of the device are primarily affected by the rate at which analyte can diffuse into and out of the indicator molecule-containing film, or, in the case of a surface coated waveguide, the rate at which analyte interacts with indicator molecules bound to the surface of the waveguide. The films employed in the present devices have large surface areas and shallow depths. Therefore, analyte can reach the site of an indicator molecule very quickly.

On the other hand, the optical signal available from the fluorescent indicator molecules is affected by the concentration of such molecules that can be placed in the path of excitation light. Since the excitation light passes transversely through fluorescent matrix film 22 or waveguide 61 from LED 20, optical efficiency is maximized.

Thus, it can be seen that the dimension responsible for optical absorption and the subsequent fluorescence is decoupled from the dimension through which the analyte of interest must diffuse into the indicator molecule-containing material. Optical absorbance is defined by Beer's law, while the rate of diffusion is defined by Fick's law. Chang, *Physical Chemistry*, pp. 64 and 147, McMillan, New York (1977). The decoupling of these two phenomena produces a device having very fast response times while maintaining a high signal-to-noise ratio.

The fluorescence sensors of this invention may be used for measuring the presence or concentration of an analyte in a liquid or gaseous medium. When used in a liquid or hostile environment, the sensor and associated electrical components may be encapsulated in an inert resin material, such as an epoxy resin, leaving only the indicator molecule-containing fluorescent matrix film 22 (or coated waveguide material 61) exposed to the test medium. The sensors of this invention have a wide range of applications in industrial, medical and environmental fields. Examples of such applications are described in U.S. Pat. No. 5,517,313. A fluorescence sensor suitable for oxygen sensing is described by Colvin et al., *Johns Hopkins APL Technical Digest*, 17(4), 377–385 (1996), which is incorporated herein by reference.

The fluorescence sensors of this invention have been described in connection with certain preferred embodiments. Those skilled in the art will recognize that modifications and improvements may be made without departing from the spirit and scope of the invention as defined by the appended claims.

What is claimed is:

1. A fluorescence sensing device for determining the presence or concentration of an analyte in a liquid or gaseous medium comprises
    (a) an optical filter having substantially flat, parallel top and bottom surfaces;
    (b) a film of analyte-permeable fluorescent matrix on the top surface of the optical filter, said matrix containing fluorescent indicator molecules whose fluorescence is modulated by the presence of analyte in said film;
    (c) a light-emitting P-N semiconductor junction which emits light at a wavelength that excites fluorescence in the indicator molecules; said light-emitting P-N junction being positioned on the top surface of the optical filter such that at least a portion of the light is emitted within the fluorescent matrix in directions substantially parallel to the top surface of the optical filter; and
    (d) a photodetector on the bottom surface of the optical filter which generates an electrical signal responsive to fluorescent light emitted by said fluorescent indicator molecules;
wherein the optical filter has a relatively low absorbance for fluorescent light emitted by said fluorescent indicator molecules and a relatively high absorbance for light emitted by said light-emitting P-N junction.

2. The fluorescence sensing device of claim 1, wherein the fluorescent matrix film has a depth of from about 500 Å to about 200 microns.

3. The fluorescence sensing device of claim 1, wherein the fluorescent matrix film has a depth of from about 10 microns to about 100 microns.

4. The fluorescence sensing device of claim 1, wherein the top surface of the optical filter has a recessed area having a depth and diameter sufficient to contain the fluorescent matrix film.

5. The fluorescence sensing device of claim 1, wherein the light-emitting P-N junction is a light-emitting diode and is positioned in a pocket in the top surface of the optical filter such that the P-N junction is positioned at about the center of the thickness of the analyte-permeable material.

6. The fluorescence sensing device of claim 1 or 5, wherein a moat is cut into the top surface of the optical filter, surrounding the light-emitting P-N junction, and serves to stop the spread of the fluorescent matrix when it is applied in liquid form.

7. The fluorescence sensing device of claim 1, wherein the fluorescent matrix is a polymer which contains fluorescent indicator molecules.

8. The fluorescence sensing device of claim 7, wherein the polymer is a silcone polymer.

9. The fluorescence sensing device of claim 7, wherein the indicator molecule is the complex, tris(4,7-diphenyl-1,10-phenanthroline)ruthenium(II) perchlorate, and the fluorescence sensing device is an oxygen sensing device.

10. The fluorescence sensing device of claim 9, wherein the optical filter has a wavelength cutoff of about 610 nm.

11. A fluorescence sensing device for determining the presence or concentration of an analyte in a liquid or gaseous medium comprises
    (a) an optical filter having substantially flat, parallel top and bottom surfaces;
    (b) a film of waveguide material on the top surface of the optical filter, said waveguide material having a refractive index greater than that of said liquid or gaseous medium and said waveguide material having on the surface thereof fluorescent indictor molecules whose fluorescence is modulated by the presence of analyte;
    (c) a light-emitting P-N semiconductor junction which emits light at a wavelength that excites fluorescence in the indicator molecules; said light-emitting P-N junction being positioned on the top surface of the optical filter such that at least a portion of the light is emitted within the waveguide, such that it is largely propagated within the waveguide and excites fluorescence in the indicator molecules on the surface of the waveguide; and
    (d) a photodetector on the bottom surface of the optical filter which generates an electrical signal responsive to fluorescent light emitted by said fluorescent indicator molecules, wherein the optical filter has a relatively low absorbance for fluorescent light emitted by said fluorescent indicator molecule and a relatively high absorbance for light emitted by said light-emitting P-N junction.

* * * * *